United States Patent
Oelschlegel et al.

(10) Patent No.: US 7,968,847 B2
(45) Date of Patent: Jun. 28, 2011

(54) IDENTIFICATION MECHANISM FOR A COMPONENT ATTACHED TO A MEDICAL DEVICE

(75) Inventors: Jürgen Oelschlegel, Nürnberg (DE); Robert Standar, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 279 days.

(21) Appl. No.: 12/275,933

(22) Filed: Nov. 21, 2008

(65) Prior Publication Data
US 2009/0143664 A1 Jun. 4, 2009

(30) Foreign Application Priority Data
Nov. 28, 2007 (DE) .................. 10 2007 057 286

(51) Int. Cl.
*G01J 5/00* (2006.01)
(52) U.S. Cl. .................................................. 250/338.1
(58) Field of Classification Search ............... 250/338.1, 250/358.1, 368; 235/454, 462.01, 468
See application file for complete search history.

(56) References Cited

U.S. PATENT DOCUMENTS

| | | | |
|---|---|---|---|
| 6,354,502 B1 * | 3/2002 | Hagstrom et al. | 235/462.04 |
| 2004/0195342 A1 * | 10/2004 | Silverbrook et al. | 235/494 |
| 2004/0243120 A1 * | 12/2004 | Orszulak et al. | 606/34 |

FOREIGN PATENT DOCUMENTS

| | | |
|---|---|---|
| DE | 44 12 605 A1 | 10/1995 |
| DE | 103 44 607 A1 | 4/2004 |
| DE | 103 27 268 A1 | 1/2005 |
| DE | 10 2005 028 741 A1 | 1/2007 |

OTHER PUBLICATIONS

German Office Action dated Jun. 23, 2008 with English translation.

* cited by examiner

*Primary Examiner* — David P Porta
*Assistant Examiner* — Mark R Gaworecki
(74) *Attorney, Agent, or Firm* — Lempia Summerfield Katz LLC

(57) ABSTRACT

The invention relates to the identification of a component of a medical device. The medical device is realized for the alternative attachment of a plurality of components. By means of infrared reflection sensors an emitted signal that is reflected by an attached component is detected. The reflected signal has a shape that is characteristic of the component. The component is identified through determination by the infrared reflection sensors that detect a reflected signal. The invention allows for alternative components that can be attached to be identified efficiently and with little outlay.

15 Claims, 3 Drawing Sheets

Serial telegram for compression plate identification

IDENTIFICATION MECHANISM FOR A COMPONENT ATTACHED TO A MEDICAL DEVICE

The present patent document claims the benefit of the filing date of DE 10 2007 057 286.9, filed Nov. 28, 2007, which is hereby incorporated by reference.

BACKGROUND

The present embodiments may relate to a medical device, a component for a medical device and a method of identifying a component attached to a medical device.

In medical technology, interchangeable and/or replaceable components are used in various devices in order to guarantee an adjustment for an examination or treatment to be performed. The various devices may include, for example, recording disks or detectors for x-ray images, for which different formats are conventional depending on the recording to be performed. However, replaceable components are also used for an adjustment of the medical device to match patient characteristics for example, in mammography.

When a mammogram is performed, a compression plate is generally provided for the compression of a female breast. A rigid, inflexible compression plate is used to compress the female breast for mammography. Compression plates of this kind are frequently made of polymethyl methacrylate (PMMA).

Compression of the breast during mammography reduces the thickness of the breast tissue to be x-rayed, which may reduce scattered radiation. Additionally, the breast is distanced from the thorax for the examination, such that an examination can be performed close to the surface of the breast.

The compression of the breast is achieved by the compression device, including the rigid compression plate, being displaced relative to a support couch (table) on which the object to be examined and/or compressed is positioned. The compression of the breast and/or of the object by a rigid compression plate, for example, during a mammogram, generally does not lead to the anatomy of the female breast, which varies from patient to patient, being taken into consideration flexibly. Accordingly, the compression of the breast by a rigid compression plate generally leads to pain being caused in the patient's breast. Damage to an object to be compressed is also conceivable.

An optimally adjusted compression plate for each specific patient may be selected and made available from among a large number of different-shaped rigid compression plates that are adjusted to match different sizes and shapes of female breasts.

The mammogram used in mammography is detected automatically. The detection can be used to verify the attached compression plate and for adjustment of the configuration of the mammography device according to the characteristics of the plate. Accordingly, different compression plates are conventionally encoded with contact bridges or storage elements, with the encoding being readable via contact pins.

SUMMARY AND DESCRIPTION

The present embodiments may obviate one or more of the problems or drawbacks inherent in the related art. For example, in one embodiment, components that may be attached to medical devices may be identified.

The present embodiments relate to medical devices for which provision is made for an alternative attachment (e.g. insertion) of several components. For example, different types of compression plates may be inserted and/or plugged into a mammography device. Alternatively, an apparatus may receive different formats of x-ray plates, catapult Bucky cabinets, or x-ray detectors. The different alternative components are each provided for an examination or treatment and are realized according to the examination and/or treatment. The use of different alternative components may be necessary because of patient characteristics (e.g., height, weight, and body shape, such as female mamma) and different applications of the device (e.g. various formats of a receiving unit for receiving different body parts). The term "alternative" here means that the various components are attached at the same position on the device, which is realized for receiving one of the alternative components.

The medical device may be used for the emission of an infrared signal for a reflection by an attached component. The medical device may include several infrared reflection sensors for detecting the signal reflected by the attached component.

The signal is reflected by a reflecting area of the component. Through individualized design of the reflecting area, the shape and/or the pattern of the reflected signal is typical and/or characteristic of the component. The component may be identified through detection by the plurality of infrared reflection sensors and through determination by the detecting sensors. For example, each alternative component corresponds to one reflection pattern that is detected and assigned by the medical device to the attached component. The identification may be performed, for example, by setting bits upon successful detection and subsequently reading out the resulting bit pattern.

A pattern may be detected, for example, by a detection area in which infrared reflection sensors are arranged side by side. The arrangement then produces a field with subareas, each of which includes one photosensor.

In one embodiment, a medical device may include a component. The component may include reflectors for the reflection of infrared light. The arrangement of the reflectors is chosen according to a generated reflection pattern that is typical for the component, which can be detected by the medical device and assigned to the component.

A reflection area that substantially corresponds to a detection area of the medical device may be produced at the component. The reflection area may have sections that are reflective or non-reflective according to the typical reflection pattern for the component.

A robust and contamination-resistant encoding of replaceable components may be provided. The identification is independent of the mechanical process of attaching the component, and is thus, less prone to faults. Standard components (e.g., a reflection sensor, decimal decoder) can be used, as a result of which the realization can be achieved with little outlay. Through the selection of optical encoding as a contactless method, the advantage of a reduced space requirement, for example, in comparison with magnetic encoding (permanent magnets and reed contacts) is also achieved.

The component may include the reflection area by a label attached to the component (identification label). The label may include sections that reflect infrared light according to the typical reflection pattern. In other words, a component can be adapted for an identification by a simple identification label that can be produced cost-effectively.

In one embodiment, the medical device may include an independent mechanism for verifying the attachment of a component to be identified. For example, upon attachment of the component, a lever is actuated or a catch is engaged, and thus, a switch is actuated. Actuation of the switch signals the plugging in and/or attachment of the component. The mirror reflection sensors may be made to trigger as a function of the presence of a component. The mirror reflection sensors may be trigged when a component is attached. In other words, the mirror reflection mechanism of identification is only activated by attaching the component.

An additional optional safety measure may include attaching an infrared filter in front of the infrared reflection sensors in order to avoid triggering by electromagnetic radiation with adjacent wavelengths.

A method of identifying a component attached to a medical device according to which the component is identified by a reflection pattern that is typical for the component is provided. The identification may take place when the result of verification by an independent mechanism indicates that a component is attached.

DETAILED DESCRIPTION

Figure 1:
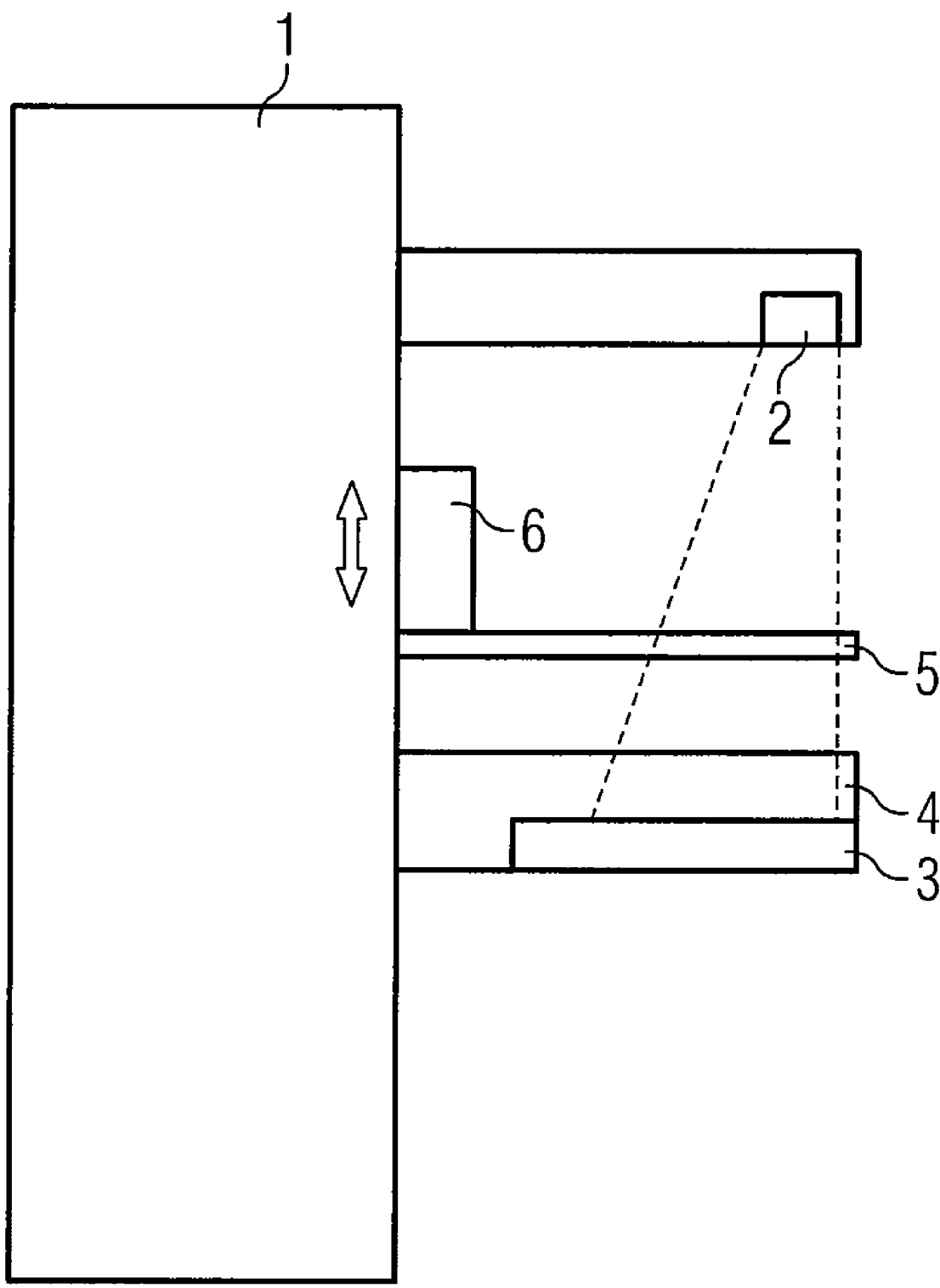
FIG. 1 shows a lateral view of one embodiment of a mammography apparatus.

FIG. 1 shows a lateral view of a mammography device. The mammography device includes an x-ray source 2 and an x-ray detector 3 for receiving x-ray images. The x-ray detector 3 is held by an object couch 4. The x-ray source 2 and the x-ray detector 3 are arranged opposite to each other by a stand 1. An adjustable compression plate 5 is provided for compression of the breast tissue to be examined. This compression plate may be replaced with compression plates of a different design and/or shape in order to enable adjustment to suit the patient. For identification, the mammography device is equipped with a printed circuit board (PCB_on which infrared reflection sensors are arranged. The PCB is arranged, for example, above the compression plate 5 in the compression unit 6 that is used for the compression. In order to keep down the wiring outlay within the compression unit 6, the optical sensors are read out sequentially with a 3-wire connection.

Figure 2:
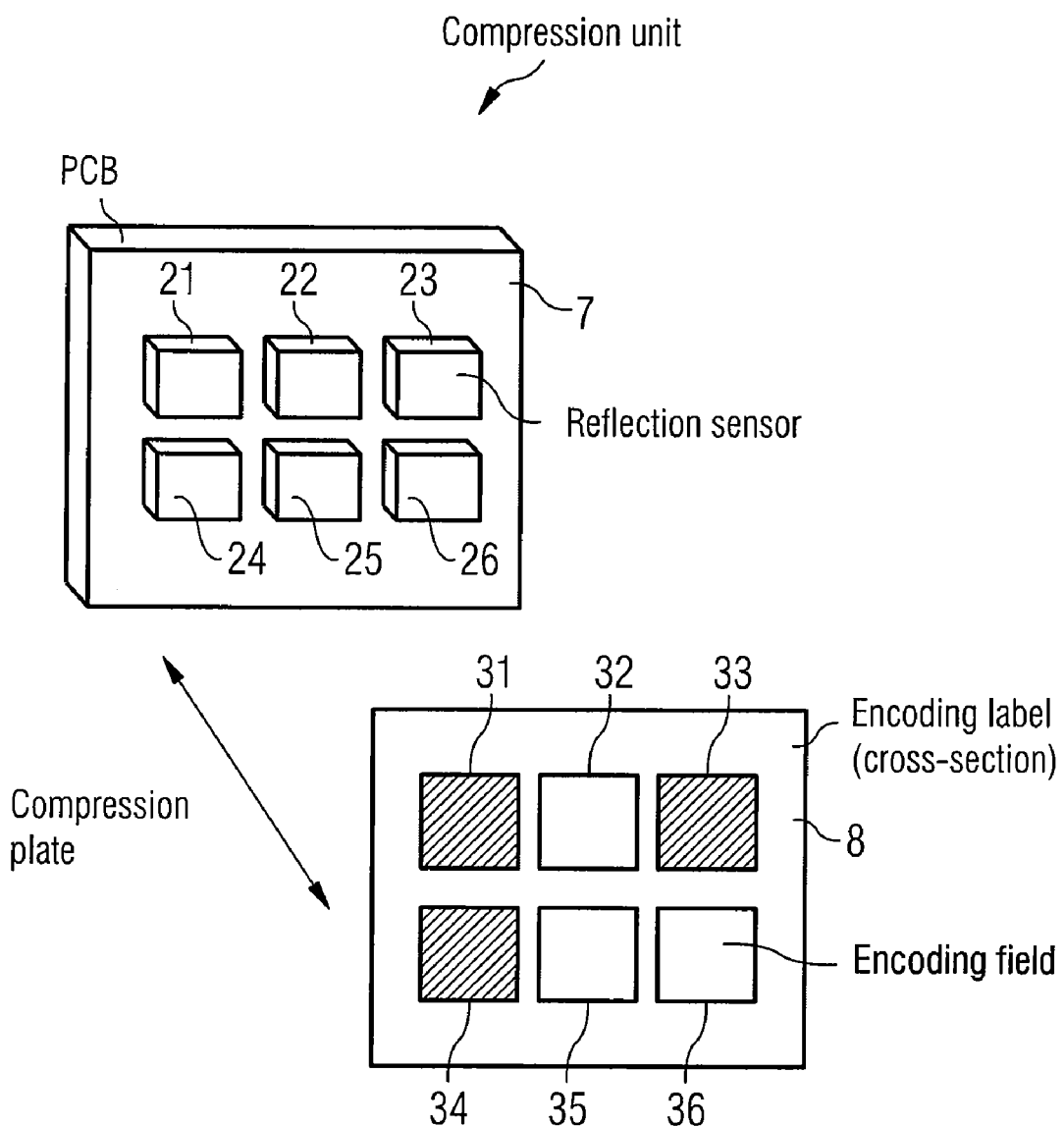
FIG. 2 shows one embodiment of a detector area and a reflection area for an identification.

FIG. 2 shows a PCB 7 with six reflection sensors 21, 22, 23, 24, 25, 26 and 27. The reflection sensors may be transmitter/detector elements so that the transmitter and receiver are arranged together spatially. FIG. 2 below shows an encoding label 8 comprising six encoding fields 31, 32, 33, 34, 35, 36 and 37. A part of the encoding fields may be reflective (e.g., 32, 35 and 36; indicated by shading). As radiation is only directed back to the detectors (infrared reflection sensors) by the reflective areas, radiation is only detected by the infrared reflection sensors 22, 25 and 26. Upon successful detection, an output of the corresponding detector is activated and/or a bit is set. A binary signal that can be interpreted as a binary number is generated by a synchronized sequential readout of this information. The binary number is decoded by a decimal decoder and assigned to a component. Components may be assigned to binary numbers and those assignments may be stored in advance.

Figure 3:
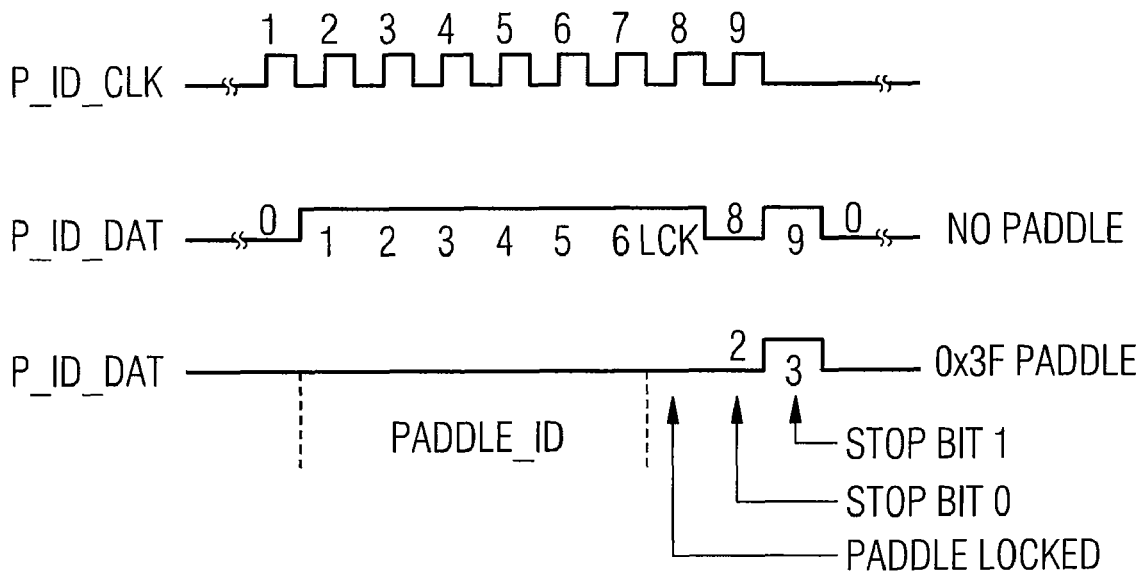
FIG. 3 shows a serial telegram for compression plate identification.

FIG. 3 shows signals that have been generated by interrogating the inputs of the decoders. The signal PID CLK provides a clock pulse for generating a binary number. A preceding 2-bit bit sequence (STOP BIT 1, STOP BIT 0) may be provided for synchronization purposes. The subsequent bit (LCK or 'paddle locked') tests whether the plate is correctly inserted. The detector inputs are read out when this bit is set to zero. In this status the compression plate is fully engaged and an interlocking switch is actuated. No scattered light can then penetrate. The readout of the bits that are present at the decoders then yields valid plate identification.

In the case of the upper signal curve for the PID DAT signal readout no compression plate (no paddle) is present. The LCK bit has a value of 1. When all six associated inputs (bits 1-6) have a value of 1, for example, no reflected light has been detected. In the case of the lower curve for PID DAT a compression plate is attached (paddle locked). The LCK bit has a value of 0, for example, identification has taken place by reflection sensors. Bits 1-6 all have a value of 0, for example, reflected infrared light was detected by all detectors. This equates to encoding of the component that reflects at all six fields (paddle ID). The bit sequence corresponds to a hexadecimal value 0x3F that can be decoded by a decimal decoder.

The present embodiments are not restricted to this exemplary embodiment. The present embodiments may be used for the identification of detectors and catapult Bucky cabinets. For example, the detection of a cassette format by distance measurement described in DE 10327268 A1 may be replaced with the method of the present embodiments.

The invention claimed is:

1. A medical instrument for the alternative attachment of a plurality of components, each of which is provided for an examination or treatment, the medical instrument comprising:
a medical device that is operable to emit an infrared signal that is reflected by an attached component, the medical device including a detection area comprising infrared reflection sensors that are operable to detect the infrared signal reflected by the attached component, such that the medical device is operable to determine one or more of the infrared reflection sensors that detect a reflected signal,
wherein the attached component comprises a reflection area comprising reflectors that reflect the infrared signal, the reflectors arranged according to a reflection pattern characteristic for the attached component that defines, for the reflection area, any combination of reflective sections and non-reflective sections,
wherein the reflection area substantially corresponds to the detection area of the medical device, and
wherein the medical device is configured to identify the attached component according to the one or more infrared reflection sensors that detect the reflected signal.

2. The medical instrument as claimed in claim 1, wherein the infrared reflection sensors are arranged side by side in the detection area.

3. The medical instrument as claimed in claim 1, wherein the medical device includes an independent mechanism configured for verifying the attachment of the attached component to be identified.

4. The medical instrument as claimed in claim 1, wherein an infrared filter is attached in front of the infrared reflection sensors.

5. The medical instrument as claimed in claim 1, wherein the medical device is a mammography device.

6. The medical instrument as claimed in claim 1, wherein the medical device is configured to set bits upon detection of the reflected signal at the one or more infrared reflection sensors and read out a resulting bit pattern to identify the attached component.

7. A component for a medical device, the component comprising:

a reflection area comprising reflectors for the reflection of infrared light, the reflectors arranged according to a reflection pattern characteristic for the component, wherein the reflection area substantially corresponds to a detection area of the medical device, the reflection area having any combination of reflective sections and non-reflective sections according to the reflection pattern characteristic for the component.

8. The component as claimed in claim 7, wherein the component includes a label attached to the component, the label comprising the reflective sections that reflect infrared light according to the reflection pattern characteristic for the component.

9. The component as claimed in claim 7, wherein the component comprises a compression plate for a mammography device, a detector for an x-ray device, or a catapult Bucky cabinet for an x-ray device.

10. The medical instrument as claimed in claim 1, wherein the attached component includes a label attached to the attached component, the label comprising the reflective sections that reflect infrared light according to the reflection pattern characteristic for the attached component.

11. The medical instrument as claimed in claim 10, wherein the attached component comprises a compression plate for a mammography device, a detector for an x-ray device, or a catapult Bucky cabinet for an x-ray device.

12. A method for the identification of a component attached to a medical device, the method comprising:

emitting an infrared signal, using the medical device, for reflection by the attached component, reflecting the infrared signal, using the attached component, to produce a reflection pattern characteristic for the attached component, detecting the reflected signal using infrared reflection sensors of the medical device, and identifying the attached component, using the medical device, according to one or more of the infrared reflection sensors that detect the reflected signal, wherein reflecting the infrared signal comprises using a reflection area of the attached component to reflect the infrared signal, the reflection area having reflective sections and non-reflective sections, and wherein detecting the reflected signal comprises using a detection area of the medical device comprising the one or more infrared reflection sensors, the detection area of the medical device substantially corresponding to the reflection area.

13. The method as claimed in claim 12, further comprising verifying the attachment of the component to be identified, wherein the component is identified only after the attachment of the component is verified.

14. The medical instrument of claim 1, wherein each of the reflective sections of the reflection area corresponds to one of the infrared reflection sensors of the detection area, and wherein each of the non-reflective sections of the reflection area corresponds to one of the infrared reflection sensors of the detection area.

15. The component of claim 7, wherein each of the reflective sections of the reflection area corresponds to one of the infrared reflection sensors of the detection area, and wherein each of the non-reflective sections of the reflection area corresponds to one of the infrared reflection sensors of the detection area.

* * * * *